United States Patent [19]

Lele

[11] Patent Number: 4,960,109

[45] Date of Patent: Oct. 2, 1990

[54] MULTI-PURPOSE TEMPERATURE SENSING PROBE FOR HYPERTHERMIA THERAPY

[75] Inventor: Padmakar P. Lele, Winchester, Mass.

[73] Assignee: Massachusetts Institute of Technology, Cambridge, Mass.

[21] Appl. No.: 209,518

[22] Filed: Jun. 21, 1988

[51] Int. Cl.$^5$ .............................................. A61B 5/00
[52] U.S. Cl. .................................... 128/736; 128/401
[58] Field of Search .................... 128/736, 804, 660.02, 128/399, 401

[56] References Cited

U.S. PATENT DOCUMENTS

| | | | |
|---|---|---|---|
| 4,228,805 | 10/1980 | Rosen et al. | 128/736 X |
| 4,311,154 | 1/1982 | Sterzer et al. | 128/736 X |
| 4,350,168 | 9/1982 | Chable et al. | 128/736 |
| 4,397,314 | 8/1983 | Vaquine | 128/399 |
| 4,620,546 | 11/1986 | Aida et al. | |
| 4,638,436 | 1/1987 | Badger | 128/736 X |
| 4,646,756 | 3/1987 | Watmough et al. | 128/804 |
| 4,658,828 | 4/1987 | Dory | |
| 4,681,122 | 7/1987 | Winters et al. | 128/736 |

Primary Examiner—Max Hindenburg
Attorney, Agent, or Firm—Thomas J. Engellenner; David A. Jacobs

[57] ABSTRACT

A multi-function probe for use in hyperthermia therapy employs at least one pair of temperature sensors, which may be thermocouples or thermistors. One sensor of the pair includes an exposed electrode which directly measures tissue temperature. The other sensor includes an electrode covered by a material having a known ultrasound absorption coefficient, for measuring the local intensity of ultrasonic energy. By comparing these two measurements, an ultrasound or other hyperthermia energy absorption coefficient of the tissue in the target region can be determined. A plurality of these paired sensors can be utilized to yield a measurement of thermal diffusion. The probe can also include one or more piezoelectric receiver elements, for providing accurate source-to-target registration.

9 Claims, 2 Drawing Sheets

MULTI-PURPOSE TEMPERATURE SENSING PROBE FOR HYPERTHERMIA THERAPY

The U.S. Government has rights in this invention pursuant to Contract Number CA 31303-03 awarded by the National Cancer Institute.

BACKGROUND OF THE INVENTION

This invention relates generally to methods and apparatus for ultrasound hyperthermia, and, more particularly, relates to apparatus and methods for measuring tissue temperature and other tissue properties in hyperthermic treatment of internal cancers and other diseases which respond to temperature elevation.

Production of a controllable level of temperature elevation or hyperthermia at pre-selected locations and volumes of tissue has been found to be of significant therapeutic value in the treatment of Patients with cancer or other diseases.

Well-managed clinical application of hyperthermia requires the ability to produce specific, well-characterized temperature elevations in precisely selected volumes of tissue that comprise the malignancy. The corresponding engineering requirement is the ability to control the temporal and spatial characteristics of the absorbed thermal dose so as to produce the desired temperature distribution for the specific malignancy being treated.

The achievement and accurate measurement of the elevated temperature distribution is thus of primary importance in any hyperthermia system. An ideal hyperthermia system would provide control of the temporal and spatial characteristics of the heat source, whether ultrasound, microwave or radio-frequency, in order to shape the volumetric power deposition pattern to the specific requirements of the malignancy.

In view of the significant tissue temperature gradients that can exist during hyperthermia as a consequence of differences in blood flow and thermal conductivity of tissue—both of which are markedly altered with temperature—and the evidence that temperature control is crucial to successful hyperthermia treatment, it is equally crucial that accurate high-resolution thermometry at multiple sites in the treatment volume be available. Temperature gradients will be greatest at the boundaries of differential energy absorption, perfusion and conductivity, and thus, the temperature at the tumor margin or proliferating edge, as well as other locations within the tumor, must be known.

The state of tissue perfusion is a primary component in local heat transport, the regulation of which is crucial to hyperthermia. Thus, planning and optimization of hyperthermia therapy requires knowledge of the distribution and magnitude of the local level of perfusion. Because blood flow has a significant influence on the temperature distribution in tissue during hyperthermia, knowledge of the magnitude and the distribution of perfusion in both the tumor and surrounding host tissue is necessary for accurate thermal therapy planning or predictive modeling of temperature distribution during hyperthermia. Additionally, information on local blood flow in the treatment volume during hyperthermia is essential to enable effective sequencing of hyperthermic and radiation therapy or chemotherapy.

It would therefore be useful to monitor temperature distributions accurately during hyperthermic treatments of cancer while minimally perturbing the local environment. It would also be desirable to provide a means for obtaining temperature measurements at a plurality of tissue locations, together with other measurements of tissue characteristics including blood perfusion, thermal conductivity and thermal diffusivity.

Furthermore, in ultrasound hyperthermia systems, it would be desirable to obtain acoustic attenuation, acoustic absorption and sound Propagation velocity data, together with information representative of the separation between the ultrasound source and the target area.

Conventional methods for temperature measurements in vivo involve the insertion of catheters or probes which contain one or more thermistors or thermocouple junctions. Such a technique is minimally invasive and, if correctly implemented, provides accurate temperature measurements in real-time.

Conventional hyperthermia probes, however, cannot provide measurements of properties other than temperature. Such apparatus, for example, cannot supply data representative of thermal diffusion, tissue perfusion, acoustic absorption, acoustic attenuation, onset of cavitation, and sound propagation velocity, essential to planning effective and safe treatment. Moreover, conventional probes for hyperthermia treatment cannot provide other useful data such as insonation head-to-probe distance, or the separation between multiple probes. In addition, conventional probes are non-flexible, and present a risk of tissue tearing due to patient movement or movement of internal organs.

Accordingly, there exists a need for hyperthermia probe apparatus and methods which can measure a variety of physical properties of the tissue, and which can be used to provide positional information to the hyperthermia system computer and the operator.

It is accordingly an object of the invention to provide improved hyperthermia probe methods and apparatus.

It is another object of the invention to provide methods and apparatus for measuring temperature, thermal diffusion, tissue perfusion, local intensity, energy absorption, onset of cavitation, and other properties in hyperthermia treatment.

It is a further object of the invention to provide a probe which can provide positional data representative of relative source, probe and tissue separations.

Other general and specific objects of the invention will in part be obvious and will in part appear hereinafter.

SUMMARY OF THE INVENTION

The foregoing objects are attained by the invention, which provides a probe for use in an ultrasonic hyperthermia system. In one aspect of the invention, the probe includes a probe body adapted for insertion into a target region of tissue within a subject during hyperthermic treatment. The probe also includes at least one pair of thermal sensors carried by the probe body and disposed in proximity to each other. Typically, it is preferable that the paired sensors be disposed adjacent to each other or within five (5) millimeters so that they both are subject to a common level of hyperthermic energy.

In accordance with this aspect of the invention, the paired sensors include a first thermal sensor for measuring the temperature of the tissue and a second thermal sensor for measuring the temperature of a standard having a known ultrasonic or other hyperthermic energy absorption characteristic. Measurements from said first and second sensors can be compared to derive the energy absorption characteristic of tissue within the target region.

In another aspect of the invention, the probe further includes at least one additional thermal sensor carried by the probe body and disposed in a spaced apart relationship to the first tissue temperature sensor, for measuring the temperature of the tissue at another location, and for deriving therefrom a measurement of thermal diffusion within the tissue.

In a further aspect of the invention, the probe also includes registration elements for registering the location of the target region in relation to an ultrasonic or other source of hyperthermic treatment. The registration elements can include an ultrasonic receiver or a pair of ultrasonic receivers separated by a known displacement, for measuring the intensity of the ultrasonic energy during hyperthermic treatment.

The invention also provides a method for measuring ultrasonic energy absorption within a target region of an ultrasonic hyperthermia system. The method includes the steps of adapting a probe body for insertion into a target region of tissue within a subject during hyperthermic treatment, and disposing at least one pair of thermal sensors on the probe body in proximity to each other.

The method also includes the steps of measuring with a first thermal sensor the temperature of the tissue, measuring with a second thermal sensor the temperature of a standard having a known ultrasonic energy absorption characteristic, and comparing measurements from the first and second sensors to derive an ultrasonic energy absorption characteristic of tissue within the target region.

In accordance with another aspect of the invention, the method includes the steps of disposing at least one additional thermal sensor on the probe body in a spaced apart relationship to the first tissue temperature sensor, measuring the temperature of the tissue at another location, and deriving therefrom a measurement of thermal diffusion within the tissue.

In a further aspect of the invention, the method further comprises the step of registering the location of the target region in relation to an ultrasonic source of hyperthermic treatment. The registering step includes the step of measuring the transit time of the ultrasonic energy from the ultrasonic heating source to receivers located on the probe.

The invention can include a flexible wire probe and a rigid inserter which is withdrawn after the probe is inserted.

The invention accordingly comprises the steps and apparatus embodying features of construction, combination of elements and arrangements of parts adapted to effect such steps, as exemplified in the following detailed disclosure, and the scope of the invention is indicated in the claims.

BRIEF DESCRIPTION OF THE DRAWINGS

For a fuller understanding of the nature and objects of the invention, reference should be made to the following detailed description and the accompanying drawings, in which.

DESCRIPTION OF PREFERRED EMBODIMENTS

Figure 1:
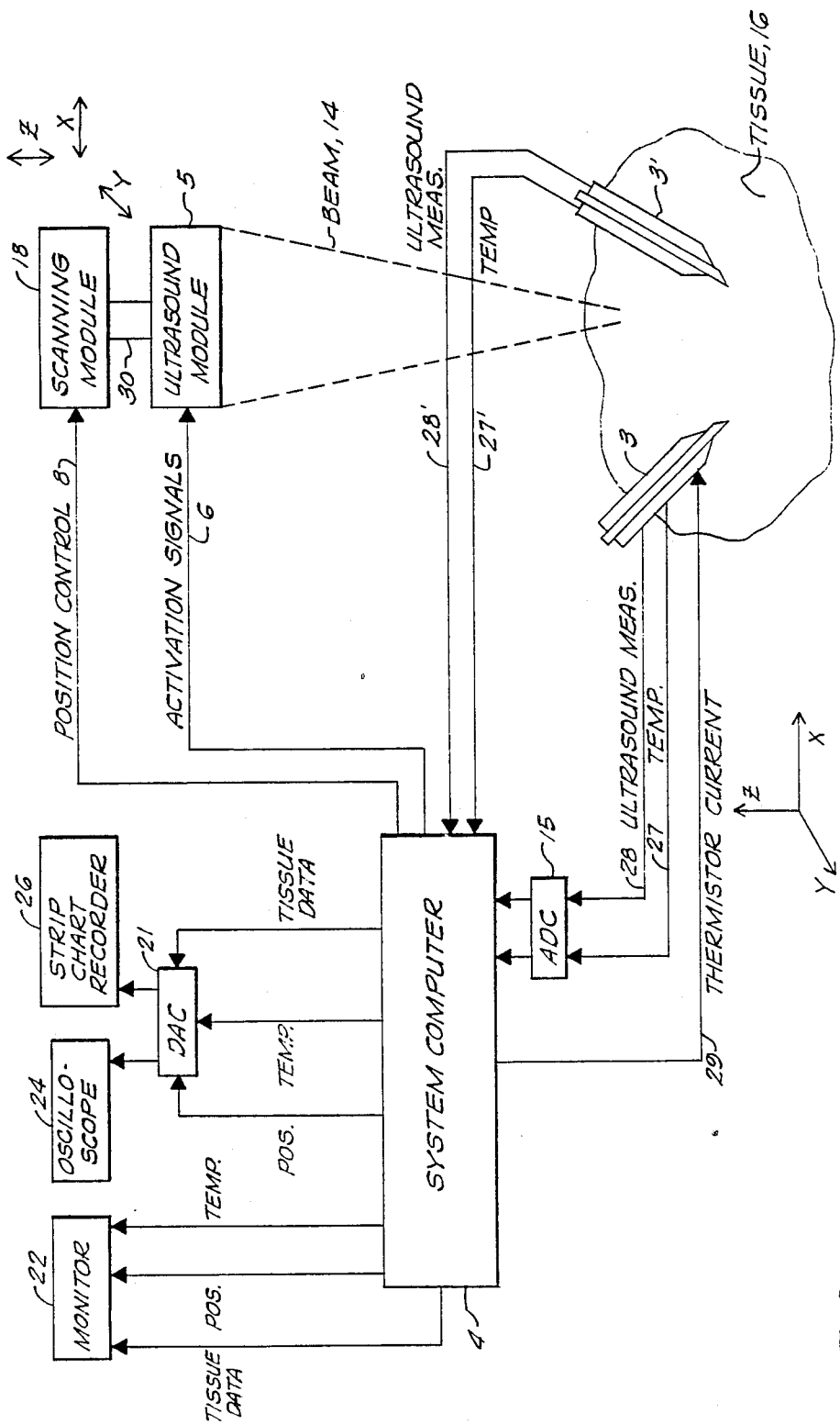
FIG. 1 depicts a hyperthermia system utilizing a multi-purpose probe in accordance with the invention.

FIG. 1 depicts a hyperthermia system 1 utilizing a number of multi-purpose probes 3,3' in accordance with the invention, for generating electrical signals 27, 27', 28, 28' representative of local temperature and applied ultrasound energy. The illustrated hyperthermia system 1 includes an ultrasound generation module 5 for generating an ultrasound beam 14 and directing the beam 14 into tissue 16. The hyperthermia system is preferably one described in commonly owned co-pending U.S. patent applications Ser. Nos. 209,520, 209,519, and 209,517 filed on even date herewith and incorporated herein by reference. The system 1 also utilizes a system computer 4, of conventional design and construction, for controlling the beam position and power output of the ultrasound generation module 5 and for processing the electrical signals 27, 27', 28, 28' generated by the probes into data displayable by a monitor 22, oscilloscope 24, strip chart recorder 26 or the like.

As FIG. 1 illustrates, the system computer 4 can generate variable activation signals 6. These signals are transmitted to ultrasound generation module 5, which responds to the activation signals 6 in a manner known in the art, D4 generating ultrasonic energy in accordance with the computer's instructions. The activation signals 6 can specify, for example, the energy level, the focal depth, the size and shape of the focal region and (when multiple ultrasonic transducers are used) the sequence of individual transducer operations.

When the invention is practiced in a hyperthermia therapy setting, ultrasound generating module 5 can be connected by coupling 30 to scanning module 18. Scanning module 18 preferably contains conventional stepper motors or servos, for generating selected X, Y and Z axis displacements in response to position control signals 8 asserted by system computer 4.

In response to the ultrasound energy of beam 14, probes 3,3' generate analog electrical signals 27, 27', 28, 28' representative of local temperature and ultrasound energy, in a manner discussed in greater detail below. The analog signals generated by probes 3,3' are converted into digital form by analog to digital converter (ADC) 15 and asserted at the inputs of system computer 4. System computer 4 reads the digital signals and processes the signals to produce temperature, probe position, and tissue data which can be displayed by a monitor 22, or, after conversion to analog form by DAC 21, by oscilloscope 24 or strip chart recorder 26. This processing is further discussed hereinafter, in connection with FIG. 2. Additionally, system computer 4 can control the application of a selected thermistor current 29 to one or more of the probes 3,3', in a manner discussed in greater detail below in connection with FIG. 2.

A probe according to the invention can be advantageously utilized in connection with the hyperthermia systems described in commonly owned, co-pending U.S. patent applications Ser. Nos. 209,520, 209,519, and 209,517 filed on even date herewith and incorporated herein by reference.

Figure 2A:
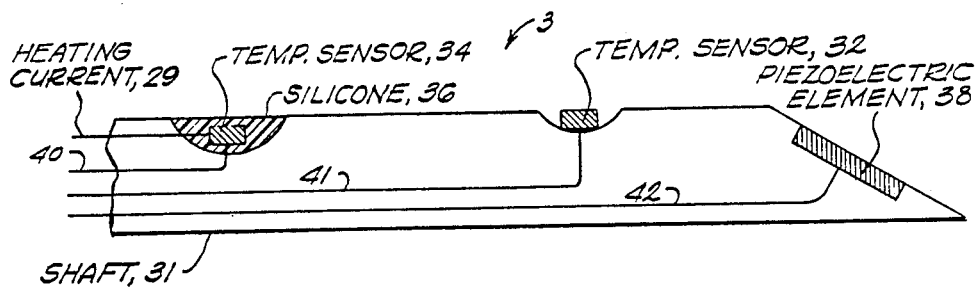
FIGS. 2A and 2B show detail of probes constructed in accordance with the invention.

FIG. 2A shows detail of a probe 3 utilized in the system of FIG. 1. In one embodiment of the invention, the probe 3 utilizes a conventional hypodermic needle element having a shaft 31. Alternatively, a flexible wire probe and rigid inserter can be utilized. The inserter is removed after the probe is inserted. The size of the probe 3, including its length and cross section, are arbitrary, and will vary according to specific application. The diameter of the probe should be sufficiently small so that it can be inserted into living tissue, including tumor tissue. A typical cross-sectional dimension will be between 100 and 1,000 microns, and the length will be between 5.0 and 20 centimeters. Additionally, the exterior of the probe 3 is preferably constructed from a material which is non-toxic to tissue, and can be for example, stainless steel. Materials are selected and the probe array is designed to provide a good thermal match to tissue.

In accordance with the invention, the probe 3 includes at least one pair of thermal sensors 32, 34, secured to the probe substrate by methods such as bonding, soldering, or polymeric adhesives. Additional thermal sensor pairs can be spaced apart, uniformly or non-uniformly as desired, along the length of the probe to provide a plurality of positions where tissue temperature can be measured. Conductive leads 40, 41 provide a conductive path from the thermal sensors to the system computer 4. The entire probe assembly 3 can be constructed from an insulating material or enclosed within an insulating material such as polyamide or epoxy resin or other biocompatible coating with insulating properties, so long as the appropriate thermal sensors are not affected.

Because apparatus according to the invention provides accurate temperature measurements at discrete locations within the tissue where the probe is inserted, the hyperthermia operator can determine whether all or only a portion of tumor tissue has achieved a sufficiently high temperature to be effective in killing tumor cells.

Examples of suitable thermal sensors include thermistors, diodes, or other P-N junctions. A preferred thermal sensor is a thermistor, which provides enhanced signal gain, higher resolution, and low noise.

In a further preferred embodiment of the invention, during steady-state thermal conditions, one or more of the thermistor sensors 32 or 34 can be heated by a thermistor current 29 and can be thereby utilized as thermal diffusion sensors. In this embodiment, the system computer 4 correlates tissue temperature with the potential measured across the thermistor created by a known current flow. The thermal electrode can be heated by using a high frequency excitation which results in appreciable resistive heating.

Electrical power supplied to the thermal sensors is regulated by any conventional means, such as an electronic control circuit, so that a predetermined mean temperature is rapidly attained and is maintained at the desired constant level above a reference temperature. Any variations in the desired temperature level are appropriately sensed so that the controller can then increase or reduce the input power to the thermal sensor to a value which maintains the temperature thereof at a desired level.

A variable voltage, which is applied to the thermal sensor, can be converted to digital form and used as digital input information to system computer 4 which is configured to calculate thermal conductivity, thermal diffusivity, perfusion, and specific thermal absorption rates. In particular, the voltage drop across each thermistor is read and converted to digital form by an analog-to-digital converter 15, and used as digital input information to system computer 4, which is arranged to calculate thermal conductivity, thermal diffusivity, perfusion and specific thermal absorption rates.

System computer 4 utilized in conjunction with the invention can be any conventional microprocessor, computer, analog circuit, computational device or the like, constructed and programmed by means known in the art to convert the electrical signals generated by the probe into temperature data, by taking into account the lead resistance, lead temperature-resistance relationship, lead temperature (computed from thermistor measurements), thermistor resistance, thermistor temperature-resistance relationship, characteristic thermistor dimensions, and the power-time relationship of heated sensors.

A method for determining thermal conductivity, thermal diffusivity and perfusion are disclosed, for example, in U.S. Pat. No. 4,059,982, which is incorporated herein by reference. Perfusion can be calculated by any method known in the art, such as those based on the bio-heat equation or simplification thereof. Such a method is taught in U.S. Pat. No. 4,059,982.

Moreover, specific thermal absorption rate (SAR) or local deposition of energy can be determined from the initial slope of the temperature-time curve, modified by multiplying by the produce of tissue density D and heat capacity C. The (D×C) product is known from the ratio of thermal conductivity K to thermal diffusivity M:DC=K/M.

System computer 4 and its associated software can be utilized to compensate for errors in tissue temperature measurements arising from the well-known phenomena of heat conduction along the probe shaft, and viscous heating of the tissue surrounding the probe when subjected to an ultrasonic field.

In a further preferred embodiment of the invention, acoustic absorption can be measured using a technique which compares the temperature-time responses of a sensor directly in contact with the tissue with that of a sensor coated with an ultrasound absorbing material of known absorption coefficient. In particular, temperature measuring element 32 is uninsulated, and directly measures tissue temperature. Another temperature measuring element 34 is disposed in a potting or sleeve of 36 of known acoustic properties. The potting or sleeve material may be silicone, and serves as a reference for the tissue absorption coefficient at the frequency used for hyperthermia. Because the absorption of the potting or sleeve 36 is known, the electrical output of the two elements 32, 34 can be compared to derive a measurement of energy absorption in the tissue.

Referring again to FIG. 2A, the probe 3 can also include at least one piezoelectric element 38. The piezoelectric element 38, which may be ceramic or PVDF material, is mounted at the probe tip or adjacent area on the shaft 31 of the probe, and can function as either an ultrasonic receiver or an ultrasonic transmitter. In particular, piezoelectric element 38 can generate an electrical signal representative of applied ultrasound energy, or an ultrasound signal representative of an applied electrical excitation.

An important feature of the invention is that piezoelectric element 38 can be utilized to provide information not only on local ultrasound intensity, but also on the position of the hyperthermia energy source relative to the probe tip in the treatment area. Probe registration, ultrasound propagation velocity, and attenuation data can be generated in accordance with conventional through-transmission principles, by using the probes and their associated piezoelectric tranducer elements as ultrasonic receivers, transmitters or reflectors.

In one practice of the invention, registration data is generated by measuring the transit time of ultrasound pulses from the hyperthermia ultrasound source to the probe, or from the probe to the source. An acoustic transmitter can be provided at the hyperthermia ultrasound source, to transmit an acoustic pulse at a predetermined time interval. This pulse is then received by the piezoelectric element 38 in the probe 3, and the signals are processed by system computer 4 to generate data representative of source-to-target registration. Alternatively, a piezoelectric transducer element in an adjacent probe can be utilized to generate ultrasonic pulses for transmit time measurement.

In another practice of the invention, ultrasonic interrogating pulses are generated at the hyperthermia energy source or at a first probe, the pulses are reflected off a second probe, and total transit time is measured to provide positional information. A passive sound reflector can be incorporated into the probe head to provide more efficient reflection for echo measurements.

An important application of the probe illustrated in FIG. 2A is continuous monitoring of the alignment of the scanning hyperthermia equipment with the tissue volume under treatment. Because the hyperthermia source transducer will scan across the treatment area during the treatment mode, multiple time delay measurements can be used for accurate localization, in three dimensions, of the receiving probe. In a preferred practice of the invention, a single probe having a single piezoelectric transducer can be used for registration. An acoustic transducer is mounted on the hyperthermia energy source for generating an interrogating pulse, and measurements are made of transit time of the pulse at various points as the insonation head scans across the treatment region.

Figure 2B:
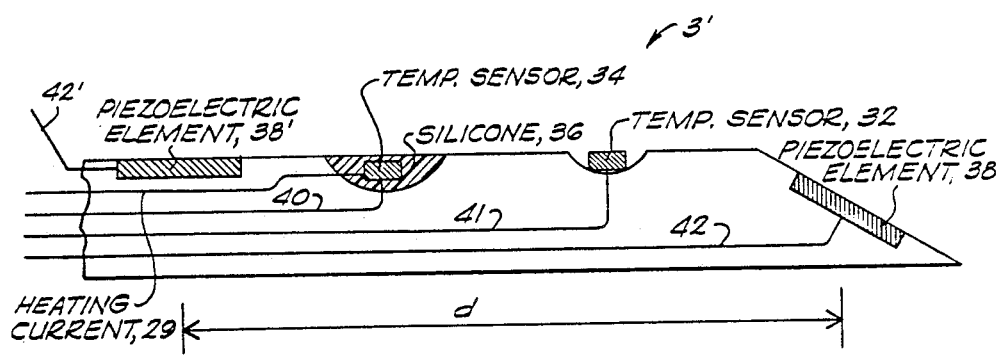

Alternatively, a single probe having at least two piezoelelectric transducers, separated by a known distance along the shaft of the probe, can be utilized to provide positional data without the necessity of scanning. Such a probe is illustrated in FIG. 2B. The illustrate probe 3' includes two piezoelectric transducer elements 38 and 38', separated by a known distance d along the probe shaft 31.

In conjunction with either of the probe embodiments illustrated in FIGS. 2A and 2B, spatial location calculations can be performed by the system computer 4, using known algorithms, and the data can be continuously available for real-time correction of scan pattern alignment. A further advantage of the invention is that because the piezoelectric transducers are highly sensitive to ultrasonic energy, far more accurate positional signals can be generated by an ultrasound transducer than by conventional temperature transducers.

In a preferred practice of the invention, the electrical output produced by the piezoelectric transducer 38 in response to applied ultrasound energy can be analyzed to detect the onset of cavitation in the surrounding tissues. Cavitation, a phenomenon familiar to those skilled in the art, can be monitored by coupling the probe output signals with conventional half-harmonic and anharmonic signal detectors.

The illustrated probe, utilized in conjunction with the insonating hyperthermia sound field, can thus measure temperature, thermal diffusion, acoustic absorption, acoustic attenuation, onset of cavitation, and sound propagation velocity. Temperature, tissue attenuation coefficients and probe-to-probe separation can be measured without the use of a hyperthermia sound field. In addition, the probe can measure hyperthermia insonation head-to-probe distance, and with the placement of more than one probe, probe-to-probe separation. These distance measurements enable the thermometric sensors to be accurately located in the tissue. Such localization is essential to both therapy planning and hyperthermia temperature distribution assessment.

It will thus be seen that the invention efficiently attains the objects set forth above, among those made apparent from the preceding description. In particular, the invention provides hyperthermia probe apparatus and methods which can measure a variety of physical properties of the tissue, and which can be used to provide accurate registration between the hyperthermia source and the target area.

It will be understood that changes may be made in the above construction and in the foregoing sequences of operation without departing from the scope of the invention. For example, while the invention has been described in connection with ultrasound hyperthermia systems, the invention can be advantageously practiced in connection with microwave, radio-frequency and other systems for generating therapeutic hyperthermia. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall there between.

Having described the invention, what is claimed as new and secured by Letters Patent is:

1. A probe for use in a hyperthermia system, the probe comprising
    a probe body adapted for insertion into a target region of tissue within a subject during hyperthermic treatment, said probe body including a region of a selected standard material having a known energy absorption characteristic, and
    at least one pair of thermal sensors carried by the probe body and disposed in proximity to each other, the paired sensors comprising
        a first thermal sensor for measuring the temperature of the tissue and
        a second thermal sensor, disposed within said standard material, for measuring the temperature of said standard material,
    whereby measurements from said first and second sensors can be compared to derive an energy absorption characteristic of tissue within the target region.

2. The probe of claim 1 wherein the probe further comprises at least one additional thermal sensor carried by the probe body and disposed in a spaced apart relationship to said first tissue temperature sensor for measuring the temperature of the tissue at another location and for deriving therefrom a measurement of thermal diffusion within the tissue.

3. The probe of claim 1 wherein the probe further comprises registration means for registering the location of the target region in relation to an ultrasonic source of hyperthermic treatment.

4. The probe of claim 3 wherein the registration means further includes at least a first ultrasonic receiver for measuring the intensity of the ultrasonic energy during hyperthermic treatment.

5. A method for measuring ultrasonic energy absorption within a target region of a hyperthermia system, the method comprising the steps of
adapting a probe body for insertion into a target region of tissue within a subject during hyperthermic treatment,
providing in said probe body a region of a selected standard material having a known energy absorption characteristic,
disposing at least one pair of thermal sensors on the probe body in proximity to each other, so that at least one of said thermal sensors is disposed in said standard material,
a measuring with a first thermal sensor the temperature of the tissue,
measuring with a second thermal sensor disposed in said standard material the temperature of said standard material, and
comparing measurements from said first and second sensors to derive an energy absorption characteristic of tissue within the target region.

6. The method of claim 5 further comprising the steps of
disposing at least one additional thermal sensor on the probe body in a spaced apart relationship to said first tissue temperature sensor,
measuring the temperature of the tissue at another location, and
deriving therefrom a measurement of thermal diffusion within the tissue.

7. The method of claim 5 wherein the method further comprises the step of registering the location of the target region in relation to an ultrasonic source of hyperthermic treatment.

8. The method of claim 7 wherein the registering step includes the step of measuring the intensity of the ultrasonic energy during hyperthermic treatment.

9. The method of claim 5 wherein the method comprises the further step of correcting for errors in thermal measurement due to any of viscous heating and heat conduction.

* * * * *